United States Patent [19]

Harmon

[11] Patent Number: 4,869,723
[45] Date of Patent: Sep. 26, 1989

[54] NATURAL FEELING CONDOM AND METHOD

[75] Inventor: James V. Harmon, Mantomedi, Minn.

[73] Assignee: Microbionics Inc, Saint Paul, Minn.

[21] Appl. No.: 83,642

[22] Filed: Aug. 10, 1987

[51] Int. Cl.⁴ ........................................ A61F 5/44
[52] U.S. Cl. ................................ 604/349; 128/844; 206/69
[58] Field of Search ................. 128/132 R, 844; 604/349, 351, 352; 206/69

[56] References Cited

U.S. PATENT DOCUMENTS

| | | | |
|---|---|---|---|
| Re. 31,454 | 12/1983 | Hymes | 128/641 |
| D. 246,117 | 10/1977 | Okamoto | 24/99 |
| D. 246,118 | 10/1977 | Okamoto | D24/99 |
| D. 246,119 | 10/1977 | Okamoto | D24/04 |
| D. 254,808 | 4/1980 | Meldahl | 128/132 R |
| 2,577,345 | 12/1951 | McEwen | 128/132 R |
| 2,586,674 | 2/1952 | Lonne | 604/349 |
| 3,136,417 | 6/1964 | Clinch | 604/349 |
| 3,339,546 | 9/1967 | Chen | 128/156 |
| 3,677,225 | 7/1972 | Czirely | 128/132 |
| 3,998,215 | 12/1976 | Anderson et al. | 128/2.06 E |
| 4,119,094 | 10/1978 | Micklus et al. | 128/132 |
| 4,274,420 | 6/1981 | Hymes | 128/641 |
| 4,306,551 | 12/1981 | Hymes et al. | 128/156 |
| 4,307,717 | 12/1981 | Hymes et al. | 128/156 |
| 4,354,494 | 10/1982 | Hogin | 128/294 |
| 4,415,548 | 11/1983 | Reddy | 424/28 |
| 4,475,910 | 10/1984 | Conway et al. | 604/352 |
| 4,638,790 | 1/1987 | Conway et al. | 128/138 |
| 4,640,688 | 2/1987 | Hauser | 604/352 |
| 4,798,600 | 1/1989 | Meadows | 604/349 |

FOREIGN PATENT DOCUMENTS

| | | |
|---|---|---|
| 2340076 | 2/1975 | Fed. Rep. of Germany . |
| 2620729 | 11/1977 | Fed. Rep. of Germany . |
| 52-138397 | 11/1977 | Japan . |
| 53-049084 | 5/1978 | Japan . |
| 53-126081 | 11/1978 | Japan . |
| 57-151329 | 9/1982 | Japan . |
| 8004357 | 6/1980 | Sweden . |
| 938465 | 10/1963 | United Kingdom | 604/349 |
| 1250553 | 10/1971 | United Kingdom | 128/132 |

*Primary Examiner*—Carroll B. Dority, Jr.

[57] ABSTRACT

A condom is provided for enhancing feeling and stimulation on the part of the male by allowing the condom to move, e.g., by a sliding action on the surface of the penis during intercourse. Typically the distal end of the condom is frictionally related to the vagina by weakly bonding the condom to the vagina as by means of a gum-like adhesive agent or by means of a multiplicity of minute fibers bonded on the outside surface of the condom or both. The condom near its open end is held tightly against the base of the penis and, if desired weakly bonded thereto by means of a removable adhesive to form a tight seal.

41 Claims, 1 Drawing Sheet

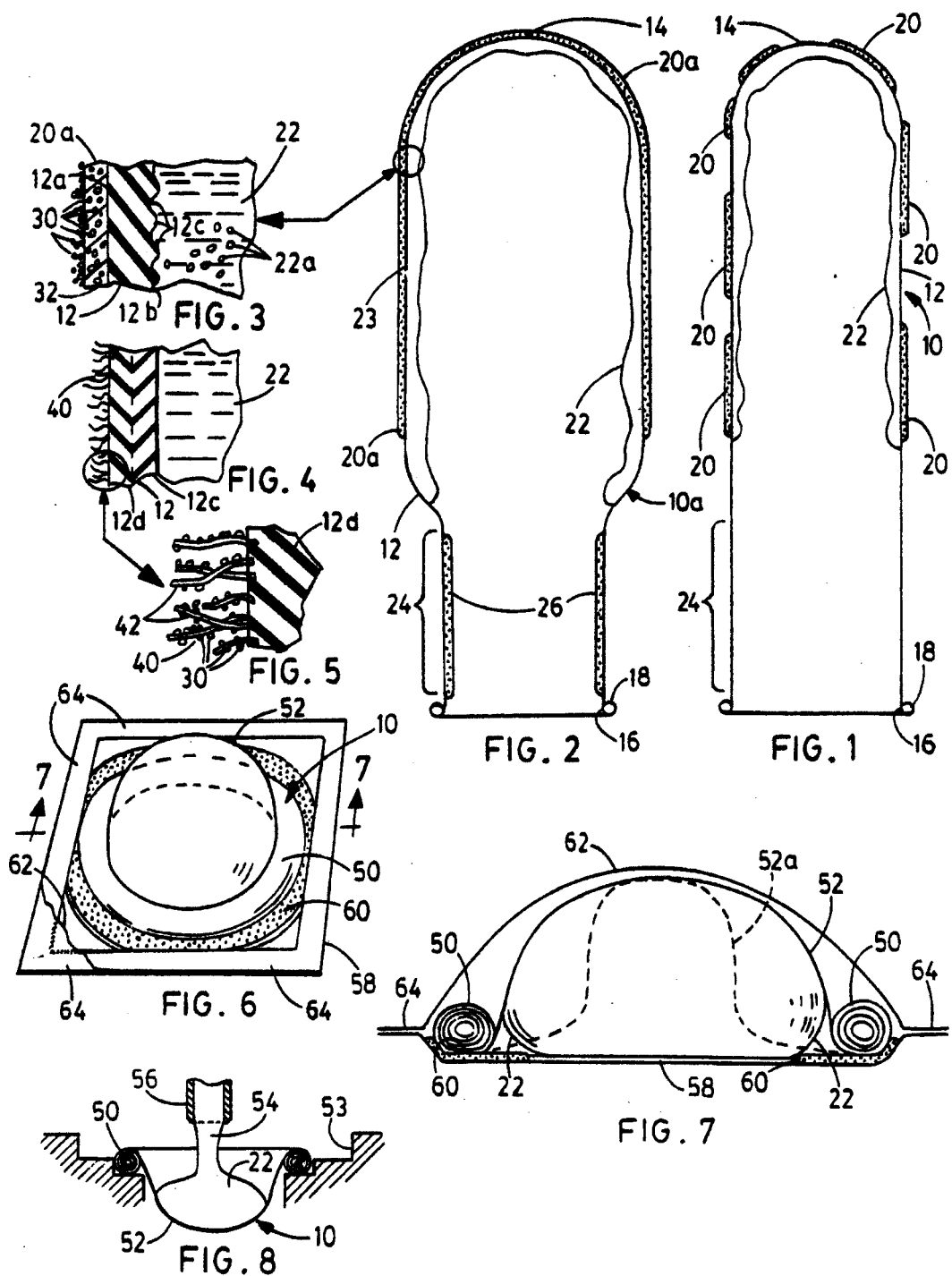

NATURAL FEELING CONDOM AND METHOD

FIELD OF THE INVENTION

The present invention relates to condoms and more particularly to a condom and method for providing a natural feeling for the male partner during intercourse while using a condom.

BACKGROUND OF THE INVENTION

While few women notice enough difference when a condom is used to avoid using one, men often avoid using condoms because they interfere with the pleasure associated with intercourse. Men complain that there is little feeling and consequently sometimes avoid using a condom even when failing to do so could have undesirable consequences or is dangerous. To overcome this problem condoms have been proposed which are either thinner or smaller in size in an attempt to help reduce the amount of interference with the natural feeling men are used to during intercourse without the use of a condom, but the objections persist.

SUMMARY OF THE INVENTION

The invention concerns a method for increasing male sensation and heightening enjoyment on the part of the male partner during intercourse while using a condom by allowing or facilitating movement of the penis within the condom during coitus to increase stimulation of the penis and provide a more natural feel similar to that when no condom is used. The condom is constructed and arranged to permit and preferably to facilitate a sliding movement of the penis inside the condom. Preferably, a friction imparting agency is provided between the condom and vagina tending to stabilized or at least partially hold the condom in place and thereby reduce or limit its movement relative to the vagina during intercourse to further facilitate movement of the penis with respect to the surrounding wall of the condom over at least a part of its inner surface so as to increase penile nerve stimulation. Nerve excitation elements can be provided, if desired, within the condom to stimulate the penis as it moves therein during intercourse. A few moments after insertion, the condom will form a frictional relationship with the moist surfaces of the vagina and in some cases will form a temporary bond with the mucosa. Movement will therefore be facilitated between the male sex organ and the aligned, i.e., corresponding inside portion of the condom. A lubricant is preferably provided between the penis and the condom to help it slide against the wall of the condom which is held in place by the frictional relationship with the vagina. This provides greater stimulation for the male and a much more natural feel than is experienced with an ordinary condom. However, the portion of the condom near the open end will remain in close or tight non-sliding contact with the base portion of the penis to provide a leak-proof seal. The unique condoms of the present invention can be made to appear almost indistinguishable from conventional condoms. They are easy to apply and use, they are supple, pliable, soft and will conform to the penis and to the vagina. They are easily moistened with water or otherwise lubricated just prior to insertion into the vagina. They are non-irritating, have no odor and are safe to use. They will also remain in place during coitus, afterward can be easily removed and have prophylactic characteristics as good as a conventional condom.

Additional features of the invention will be apparent from consideration of the accompanying specification, claims and drawings which illustrate by way of example but a few of the various ways in which the invention can be accomplished.

THE FIGURES

FIG. 1 is a semi-diagrammatic longitudinal sectional view of one preferred form of condom embodying the present invention.

FIG. 2 is a view similar to FIG. 1 showing another embodiment.

FIG. 3 is a greatly magnified or microscopic view of a small portion of the wall of the condom of FIG. 2.

FIG. 4 is a microscopic view similar to FIG. 3 of another embodiment of the invention.

FIG. 5 is a microscopic view similar to FIGS. 3 and 4 of still another embodiment of the invention.

FIG. 6 is a perspective view of a sealed package containing a lubricated condom in accordance with a preferred form of the invention in which almost all of the upper sheet of the packaging envelope has been removed so that the contents can be easily seen.

FIG. 7 is a vertical sectional view taken on line 7—7 of FIG. 6 on a somewhat enlarged scale, and FIG. 8 is a diagrammatic vertical sectional view showing how the condom is filled with a lubricant prior to packaging in one preferred form of the invention.

DETAILED DESCRIPTION OF THE INVENTION

Shown in FIG. 1 is a condom 10 having a supple sheath-like condom body 12 that is closed at one end 14 and open at the other end 16. The open end 16 preferably has a conventional beaded edge 18. The condom body 12 can be formed from the usual materials such as cured rubber latex or other supple material, e.g., sheep caecum. For convenience the invention will be described in connection with a rolled rubber latex condom although rubber is not an essential component of the invention.

The condom body 12 is conventional in thickness, e.g., typically between about 0.002 and 0.006 inches in thickness. It can, however, be much thicker and consequently stronger than an ordinary condom without adversely affecting the enjoyment of the male partner as will be apparent from the following description.

On the outside surface of the condom body 12 is provided a friction imparting agent which is deposited in several spaced apart patches or bands 20 that together cover the distal end of the condom, i.e., the portion adjacent the closed end 14. The thickness of the patches 20 has been greatly exaggerated for illustration only. Actually, the invention has almost the same appearance as a conventional condom. The friction imparting agent 20 functions to produce friction between the condom and the vagina, tending to stabilized or at least partially hold the condom in place or limit its movement relative to the vagina during intercourse. This will facilitate motion of the penis with respect to the surrounding wall of the condom over at least a portion of the inner surface of the condom to thereby increase penile nerve stimulation due to the rubbing action between the condom 10 and the penis. Movement is facilitated if a lubricant 22, e.g., any commercially available lubricant with or without spermacide, is provided within the condom 10 either by introducing it as from a collapsible tube (not shown) just prior to use or by providing the lubricant 22 within the condom when the condom is packaged.

The condom 10 is of conventional size and is of uniform diameter throughout. The base portion 24 of the condom 10 has a tight fit on the penis to make a seal for preventing leakage during normal use. The friction imparting agent 20 to be described in more detail below can comprise either a hydrophilic gel or other bonding agency or a fibrous material to produce friction between the sheath 12 and the wall of the vagina.

Refer now to FIGS. 2 and 3 which illustrate another embodiment of the invention wherein the same numerals refer to corresponding parts already described. The condom 10a of FIG. 2 has a distal portion 23 of a relatively large diameter and a proximal portion 24 of a smaller diameter. While obviously human needs vary, the proximal portion 24 can have a diameter of about 1½ inches (2 inches when flat) and the distal portion 23 about 2 inches in diameter (3 inches flat width). This will tend to make the distal end looser around the penis than the sheath 12 of FIG. 1, facilitating even more movement between the condom and the penis. Thus, while the distal end of the condom 10 of FIG. 1 will slide on the penis owing to the action of the friction imparting agent patches 20 which tend to hold it in place within the vagina, it is even easier in the embodiment of FIG. 2 for the distal end of the penis to slide within the distal end portion 23 of the condom 10a owing to its larger size.

A friction imparting agent 20a is applied to the outside surface of the distal portion 23 of the condom 10a. The agent 20a can be of any of the compositions described below or of other suitable composition but in this case is applied over the entire surface so as to impart friction between the vagina and the condom 10a.

Within the condom 10a in the reduced diameter proximal portion 24 adjacent the open end 16 is applied an optional layer of pressure sensitive adhesive 26 that covers the entire inside of the end portion 24. The adhesive 26 can comprise any well known sticky surgical grade adhesive or other pressure-sensitive adhesive known to the art applied by any conventional means, for example as described in U.S. Pat. Nos. 4,638,790 or 4,475,910 except that the adhesive 26 is located close to the open end 16. Adhesive 26 can be applied by other means. If desired, the adhesive 26 can be applied to a molding form used to produce the condom 10a prior to dipping the form in liquid latex rubber. It can also be applied to the condom by turning portion 24 inside-out. Unlike the adhesive in the aforesaid patents, the adhesive band 26 of the present invention is located adjacent to the open end 16 of the condom 10a. The entire remaining distal portion of the condom, in this case over half of the condom, is free and is able to move relative to the penis.

In both FIGS. 1 and 2 there is provided a condom having two zones on the inside, namely, a fixed zone 24 in the proximal region adjacent the open end 16 of the condom which is tight against the penis to form a stationary leak-proof seal around the base of the penis and a free zone above the zone 24 adjacent the closed end which is sufficiently loose to slide on the distal end of the penis especially when the lubricant 22 is present between the condom and the penis to thereby stimulate the penis due to the rubbing action between the free portion of the condom and the penis. The friction with the vaginal wall outside is thus greater than that inside the distal portion 23.

The wall of the condom 10a is shown greatly magnified in the microscopic view of FIG. 3. The wall 12 of the condom itself is in this case made of cured rubber latex. Inside is the lubricant 22 which can comprise any suitable condom lubricant known in the art. Outside the rubber layer 12 is the friction imparting agency 20a of the same type as designated 20 in FIG. 1. The length of the condom 10a is preferably 2 or 3 inches longer than a regular condom so that folds can form during use just distally of the fixed or tight portion, i.e., portion 24, to provide a total length of say about 10 to 11 inches allowing the closed end 14 to slide off of and onto the penis.

The friction imparting agent agency 20a will now be described in more detail. One preferred friction imparting agency comprises a hydrocolloid gum in a dry, i.e., unhydrated state. The gum is shown as a powder composed of minute particles 30 some of which are exposed at the surface and some of which are imbedded in a matrix 32 that helps to produce friction in the vagina as well as to bond the gum particles 30 to the surface 12a of the wall 12 of the condom. Among the suitable gums 30 that can be used are a variety of hydrophilic hydrocolloids initially in a dry, unhydrated state and present as a fine powder that swells when exposed to the moisture of the vagina to form a thick or tough mass which resists further hydration and acts as an adhesive or friction imparting agent. Of the various suitable gums are guar gum, gum acacia, gum tragacanth, karaya, carboxymethylcellulose, carboxypropylcellulose, polyvinylalcohol, gelatin, powdered pectin, carboxypolymethylene and other water soluble or swellable hydrocolloids and mixtures thereof. The hydrocolloid gum can be adhered to the surface 12a of the sheath 12 directly if desired but it is preferred to disperse the hydrocolloid in the matrix 32 which is bonded to the condom.

The matrix 32 which holds the hydrocolloid to the outside of the condom can comprise any of a variety of natural or synthetic viscous rubbery substances such as polyisobutylene, natural rubber, rubber latex, acrylonitrile rubber, polyurethane rubber, silicone rubber and the like. The matrix 32 can also be an aqueous solution of a hydrophilic gum such as pectin. One rubbery matrix is polyisobutylene to which powdered karaya, guar or carboxymethylcellulose or a mixture thereof has been uniformly intermixed. The gums are added to the warmed rubbery matrix in a dry powdered unhydrated state. To thin composition for application to the surface of the condom, it is diluted with a suitable organic solvent such as a ketone containing solvent, lacquer thinner or other suitable organic solvent. The matrix 32 can be applied in any suitable manner as by dipping, spraying, brushing and the like. After or during solvent evaporation, it is preferred that additional gum particles 30 be applied to the still tacky outer surface of the matrix 32. This will function to prevent adjacent condom layers from adhering together when the condom is rolled up for packaging and will also provide an additional bonding or friction imparting function between the condom and the vagina. The thickness of the matrix 32 is not critical but can be on the same order as the thickness of the rubber layer 12 or thinner.

Because the feeling experienced by the male partner does not depend upon the condom being thin, the wall thickness 12 and 20a together can be as great as necessary for strength and need not be limited by attempting to induce sensation or feeling through the wall of the condom itself.

While the friction imparting coatings 20 and 20a can be prepared in various ways, good results can be obtained as follows with all quantities expressed on a volume basis. In one product the layer 20a consisted of three parts polyisobutylene (PIB) diluted with three parts of an organic solvent and mixed with one part karaya and one part carboxymethyl cellulose CMC. This was brushed onto a dry latex condom. After the solvent was partly evaporated, a dusting mixture of equal parts of powdered CMC, karaya and guar gum was, dusted onto and worked into the surface. In another product sample, after the rubber and gum mixture diluted with lacquer thinner was applied to a dry latex condom by brushing, it was partially dried for thirty seconds with a hot air dryer and rolled in dry karaya powder to form a three-layer structure as shown in FIG. 3, the outermost layer being free particles of karaya. Adhesion to the mucosa was good and the layer 20a did not delaminate from the wall 12 of the condom. The condom remained bonded to the mucosa after ten minutes and remained bonded even though agitated. In separate sample product each gum was used alone as a dusting powder. Guar appeared to form the weakest bond, CMC was next, gelatin the next greatest and karaya appeared to form the strongest bond. In another run, two parts of a pectin solution, i.e., Certo ®, were mixed with one part CMC and one part karaya and brushed on a dry latex condom. While workable, adhesion to the latex condom surface was not as long lasting. To add additional tack to the latter composition a quantity, e.g., 8 percent, of a tackifier composed of equal parts glycerine and vinyl acetate polymer based latex dispersion (Flexbond 150, Air Products, Inc., of Allentown, Pa.), can be added. In still another sample product, a thin layer of a sectic solution, i.e. Certo ® was applied to a latex condom and dusted with karaya. Bonding to the mucosa was good but after a few minutes some of the Certo ® delaminated from the condom surface.

In a preferred form of the invention the inside wall 12b of the sheath 12 is provided with a means for providing greater feeling for the male by enhancing penile nerve stimulation when the penis moves relative to the inner surface of the sheath 12 during sexual intercourse. The stimulation means in this case comprises surface irregularities 12c, i.e., ridges and grooves or pits and/or mounds in the inside surface 12b of the condom or even fibers, e.g., 1/32 inch cotton fibers bonded to project from the inner surface of the sheath to provide a velvet-like feel when used with lubricant 22. The surface irregularities thus provide the interior surface 12b with a nerve stimulating texture or surface-feel. Irregularities 12c do not have to be great in height but can be about the same size as the irregularities of the human epithelium such as the ridges that produce a fingerprint or the projections on the surface of the tongue. The irregularities shown at 12c can be made in various ways as, for example, by producing surface irregularities in the molding mandrel used to mold the condom, e.g., by shot peening the mandrel or by drilling pits in the surface, etc., the end result being a surface 12b which because of the irregularities present will add to the stimulation of the penis and help provide a natural feel when the penis moves against it during coitus. Surface irregularities are not essential to the invention; the condom 10 of FIG. 1 has a smooth interior surface similar to an ordinary condom but feeling will nevertheless be enhanced by the rubbing action of the penis against the wall of the condom. Nerve stimulation can be enhanced by other forms of nerve stimulating elements such as nerve stimulating particles, e.g., starch granules or rubber microspheres 22a dispersed in the lubricant 22.

The condom of FIG. 2 can also be made by providing a releasing, e.g., Teflon ® molding mandrel. First, the mandrel is coated with a solvent diluted PIB and gum composition and allowed to dry. A release layer such as silicone is applied over this coating and the mandrel is then dipped in latex to form the condom which is then cured and rolled. However, upon unrolling, the PIB gum composition will stick to the outside of the sheath due to its contact with the cured latex rubber and the release layer will be on the inside of the condom. If adhesive layer 26 is to be used, layer 26 is also coated onto the mandrel and allowed to dry. However, the outside thereof is not coated with silicone. Instead, the aligned outside surface of the overlying condom layer formed in the subsequent dipping operation is coated with silicone so that when unrolled, adhesive 26 will be on the inside of the condom and not transfer to the outside like layer 20a.

Refer now to FIG. 4 which illustrates a microscopic view of a modified form of the invention. In this form, the condom wall 12 is formed by dipping a molding mandrel (not shown) twice in liquid latex rubber to provide an inner layer 12c which, following removal from the latex, is completely or partially cured whereupon it is dipped again to provide a second layer 12d. Following removal from the liquid latex, a layer of minute fibers such as cotton microfibers 40 are brought in contact with the second latex layer 12d which serves as a bonding layer for adhering the minute fibers 40 to the outside surface of the condom to provide a fine, almost invisible fibrous layer over all or portions of the distal end of the condom in the same area occupied by the layers 20 or 20a of FIGS. 1 and 2. The fibers 40 can be provided by the well-known process of flocking, i.e., by dispersing the fibers in air and allowing the air to carry the fibers onto the sticky surface 12d where they adhere. The fibers 40 which are colorless form an almost imperceptible velvet-like coating at the distal end of the condom. While various kinds of fibers can be used, one suitable fiber is a chopped cotton/linen fiber sold under the name 403 Microfibers by Gougeon Brothers, Inc., Bay City, Mich. Other suitable fibers can be used such as strips or circles of woven or nonwoven cloth or fabric or patches of porous nonwoven fabric or lightweight paper such as lens paper or rice paper. One product was produced by coating the outside of a cured latex condom with a thin layer of a clear silicone rubber adhesive, General Electric Co., and dusting on 1/64 to 1/32 inch chopped cotton and linen fibers and allowing the adhesive to cure. The fibrous layer 40 can be applied in any of a variety of other ways. For example, layer 40 can carry its own pressure-sensitive adhesive (not shown) or a layer of adhesive, e.g., latex emulsion, can be applied to an ordinary condom after which a layer of fibers, fine cloth, fabric, wet strength paper or other fibrous material is applied.

The fibrous layer 40 of FIG. 4 will function as another agency for creating a frictional relationship between the condom and the vagina and can be used alone as shown in FIG. 4 or if desired can also be used with a friction imparting agency such as a hydrocolloid gum as shown in FIG. 5. In FIG. 5 the individual fibers 42 of the fibrous layer 40 are coated with particles 30 of the hydrocolloid gum described above in connection with FIG. 3. The fibers 42 can be coated in a variety of ways. For example, the fibers 42 can be exposed to a moist atmosphere and the hydrocolloid gum then dusted on the surface to provide a bond with the fibers 42. Alternatively, a suitable adhesive can be applied to the fibers before the gum particles 30 are applied. For example, polyisobutylene or other matrix can be dissolved in any suitable solvent and applied to the fibers by spraying, after which the hydrocolloid gum is dusted onto the surface and held in place on individual fibers 42 as shown in FIG. 5 by the matrix (not shown). Friction is established in two ways in this case, namely, by the fibers 42 themselves through a mechanical interlocking with the mucosa and also by the swelling of the hydrocolloidal gum particles which thicken the fluid of the vagina to augment the friction imparted by the fibers 42 of the fibrous layer 40.

Other friction enchancing agents can also be used in place of those already described such as an astringent or an acid, a base or other pH modifier to convert the proteins in the vaginal fluid from a sol to a gel state by shifting the pH toward the isoelectric point of the proteins present to reduce their solubility and thereby make the vaginal fluid more viscous. This agency can also be combined with the others described if desired.

One preferred form of packaging will now be described. In FIG. 8 a latex condom 10, which is partially rolled up at 50 so that the end portion provides an inwardly facing cup 52, is placed in a suitable circular recess within a packaging jig 53 and a stream of lubricant 22 is introduced to the inside of the condom through a pipette 56. The lubricant 22 contains moisture in this case which should be isolated from the hydrocolloid gum particles 30. To accomplish this, a sheet 58 which forms half of packaging envelope is provided with a ring 60 of releasable pressure-sensitive adhesive properly positioned to adhere to the roll 50 after the lubricant 22 is introduced. This is accomplished by introducing the sheet 58 into the jig 53 which is shaped to align the ring 60 with the roll 50 after which pressure is applied to form a releasable bond between the roll 50 and the ring 60 of pressure-sensitive adhesive. The releasable adhesive 60 can have a composition similar to what is known commonly as "contact adhesive" which is not particularly sticky, or it may have the same formulation as the adhesive used in Post-It ® Brand notes manufactured by 3M, St. Paul, Minn., which has the capability of sticking securely but allows easy removal after storage. Finally, a top packaging sheet 62 is sealed to sheet 58 by means of a peripheral edge seal 64. In this way, the lubricant 22 within the cup-shaped end portion 52 of the condom is reliably sealed in place by the removable adhesive layer 60 and will not be able to contact the gum 30 or other bonding agency in the roll 50. If desired, the end of the condom can be provided in the alternative with a reduced diameter reservoir end 52a of known construction.

Special directions are given to provide a natural feel: (1) Remove condom from container; (2) Use condom or fingers to spread lubricant over the end of penis; (3) Unroll normally; (4) Wet condom with water if desired to aid insertion.

The lubricant 22 can be of various compositions, however good results have been obtained with K.Y. ® jelly diluted with an equal volume of water. In the alternative solid lubricants such as talc, cornstarch, mica and mixtures thereof can be used within the condom if desired. Solid lubricants should also be kept separate from the friction imparting agency on the outside of the condom but the adhesive layer 60 is not considered necessary for this purpose. Obviously, the lubricant 22 whether dry or of the liquid type can be applied to the inside of the condom just before use as, for example, by squeezing it from a collapsible tube and need not be prepackaged in the condom as shown in FIGS. 7 and 8, but the latter is preferred because it provides greater reliability.

Many variations of the invention within the scope of the following claims will be apparent to those skilled in the art once the principles described above are understood.

What is claimed is:

1. A method of providing heightened male sensation while using a condom in sexual intercourse, the sensation simulating intercourse without a condom, said condom having a sealing portion near the open end and a sliding portion near the closed end, said method comprising, providing means facilitating movement of the penis within the sliding portion of the condom, said means comprises a friction imparting composition as a layer on the exterior of the sliding portion of the condom, controlling the relative amounts of the friction inside and outside of the sliding portion of the condom to maintain a friction differential in which said layer on the outside of the condom provides friction between the condom and vagina that is greater than between the penis and the condom to thereby increase penile stimulation and provide a greater sense of feeling due a rubbing action between the sliding portion of the condom and the penis.

2. The method of claim 1 wherein a friction imparting agency is provided between the condom and the vagina tending to at least partially hold the condom in place in the vagina during coitus and thereby facilitate said movement.

3. A method of providing heightened male sensation while using a condom in sexual intercourse, the sensation simulating intercourse without a condom, said condom having a sealing portion near the open end and a sliding portion near the closed end, said method comprising, providing means facilitating movement of the penis within the sliding portion of the condom to thereby increase penile stimulation and provide a greater sense of feeling due to a rubbing action between the sliding portion of the condom and the penis, said means for facilitating movement comprises a friction imparting coating on the exterior of the condom and a nerve stimulating agency comprising stimulation elements is provided within the condom and is adapted to contact the penis to stimulate the nerve endings of the penis as the penis moves relative to the condom.

4. A method for increasing male sensation during intercourse while using a condom having a wall portion comprising, providing a friction imparting agency between the wall portion of the condom and the vagina tending to at least partially hold the wall of the condom in place or limit its movement relative to the vagina during intercourse to facilitate motion of the penis with respect to the wall of the condom in at least a portion of the condom and thereby increase penile nerve stimulation and the friction imparting agency is a hydrocolloid applied to the outside surface of the condom.

5. A method for increasing male sensation during intercourse while using a condom having a wall portion comprising, providing a friction imparting agency between the wall portion of the condom and the vagina tending to at least partially hold the wall of the condom in place or limit its movement relative to the vagina during intercourse to facilitate motion of the penis with respect to the wall of the condom in at least a portion of the condom and thereby increase penile nerve stimulation and a lubricant is provided within the condom to facilitate slippage and a plurality of nerve stimulation elements are provided on the inside wall of the condom.

6. The method of claim 1 wherein a proximal portion of said condom is adhesively bonded to the base of the penis to promote a seal.

7. A male stimulating condom comprising a condom body having an inside and an outside, lubricant means inside the condom during use to promote slippage of the penis therein and an adhesion producing means as a coating on the outside of the condom to retard slippage between the vagina and the condom.

8. A male stimulating condom comprising a condom body having an inside and an outside, means inside the condom to promote slippage of the penis therein and means outside of the condom to retard slippage between the vagina and the condom and the means to retard slippage comprises a layer of a hydrocolloid in a dry, swellable particulate form applied to the outside of the condom.

9. The condom of claim 8 wherein the hydrocolloid is bonded to the condom with a layer of a viscous rubbery matrix.

10. A male stimulating condom comprising a flexible sheath closed at one end, means on the outside of the condom to frictionally relate the condom to the vagina, means to facilitate sliding of the penis internally within the condom to produce a rubbing action between the penis and the condom thereby providing a greater sense of feeling on the part of the male, and the means to facilitate sliding of the penis comprises a liquid or solid lubricant and the means to frictionally relate the condom to the vagina comprises a member selected from the group consisting of an adhesive agency, a pH modifying composition to thicken the vaginal fluid, an astringent and a multiplicity of fibers on the outer surface of the condom.

11. A male stimulating condom comprising a flexible sheath closed at one end, means on the outside of the condom to frictionally relate the condom to the vagina, means to facilitate sliding of the penis internally within the condom to produce a rubbing action between the penis and the condom thereby providing a greater sense of feeling on the part of the male, the means to facilitate sliding of the penis comprises a liquid or solid lubricant and fibers bonded to the outside surface of the condom to provide a flocked surface defining a velvet-like layer.

12. The composition of claim 11 wherein a hydrocolloid is placed on said fibers.

13. A condom for enhancing penile stimulation comprising a condom sheath having a closed end and an open with two zones including a tight zone adjacent the open end adapted to conform closely to the penis to form a leak-resistant seal around the base of the penis and a free larger zone adjacent the closed end sufficiently loose to slide on the distal end of the penis during intercourse to stimulate the penis due to the rubbing action between the free zone of the condom and the penis, the tight zone has an adhesive therein releasably bonded to the penis so as to stick to the penis during intercourse to aid in producing said leak-resistant seal and a lubricant is packaged within the free zone to promote movement thereof on the penis but the lubricant is not packaged in the tight zone.

14. An improved condom for providing greater penile stimulation comprising, an elongated hollow condom body closed at one end and open at the other end and formed from a supple sheet material, a multiplicity of internal stimulation elements therein and located during use adjacent to or in contact with the penis, said condom being constructed and arranged to permit at least the distal end of the penis to slide internally within the condom to thereby provide a greater stimulation of the penis owing to the motion of the condom relative to the penis and the resultant sliding motion of the stimulation elements over the surface of the penis and the stimulation elements comprise a multiplicity of free particles located within the condom.

15. A male stimulating condom body with at least one water soluble or swellable natural or synthetic hydrocolloid on the exterior thereof to provide sufficient friction when exposed to moisture within the vagina to stabilize the condom in the vagina and thereby tend to hold the condom to the wall of the vagina during intercourse thereby promoting movement of the penis within the condom.

16. The condom of claim 15 wherein the soluble or swellable hydrocolloid is bonded to the condom with an adhesive matrix.

17. The condom of claim 16 wherein the adhesive matrix comprises a viscous rubbery composition having said hydrocolloid dispersed therein in particulate form.

18. A male stimulating condom comprising a condom body with a multiplicity of fibers on the exterior thereof to provide sufficient friction to tend to stabilize the condom in the vagina and thereby tend to hold the condom to the wall of the vagina during intercourse and allow the penis to move within the condom.

19. The condom of claim 18 wherein the fibers comprise a multiplicity of individual fibers bonded to the surface of the condom to form a velvet-like surface layer.

20. A male stimulating condom comprising a sheath having a closed end and an open end, means on the outside surface of the condom to promote friction between the condom and the vagina thereby tending to hold the condom therein during intercourse and male stimulation elements between the inside of the condom and the penis to enhance penile nerve stimulation when the penis moves relative to the inner surface of the condom during sexual intercourse, the means on the outside of the condom comprises a composition including a water soluble or swellable hydrocolloid and a water insoluble elastic matrix.

21. The condom of claim 20 wherein said bonding composition is dusted with an outer layer of additional particles of hydrocolloid.

22. A male stimulating condom comprising,
(a) a dual diameter sheat having an open end and a closed end,
(b) said sheath being constructed and arranged such that a portion slided on the penis during intercourse,
(c) said sheath in a region adjacent the closed end being of an enlarged diameter so as to be loose on the penis and also having a composition applied to its outside surface, said composition enhancing friction between the vagina and the condom to facilitate a sliding action between the enlarged portion of the condom and the adjacent surface of the penis during intercourse, (d) a lubricant means therein during use for enhancing penile movement and hence penile stimulation adjacent the closed end responsive to the sliding action, and (e) the open end of said condom being of a smaller diameter and sufficiently close-fitting to inhibit leakage.

23. A male stimulating condom comprising, (a) a dual diameter sheath having an open end and a closed end, (b) said sheath being constructed and arranged such that a portion slides on the penis during intercourse, (c) said sheath in a region adjacent the closed end being of an enlarged diameter so as to be loose on the penis to facilitate a sliding action between the enlarged portion of the condom and the adjacent surface of the penis during intercourse, (d) the open end of said condom being of a smaller diameter and sufficiently close-fitting to inhibit leakage, (e) a high friction bonding layer therein only in proximity to the open end to promote adhesion with the base of the penis to thereby assist in holding the condom on the penis only in proximity to said open end to prevent leakage such that the enlarged diameter region is able to slide on the penis and a vaginal friction enhancing agency is present on the outside of only the enlarged portion.

24. A male stimulating condom comprising a flexible sheath closed at one end, means on the outside of the condom to frictionally relate the condom to the vagina, means to facilitate sliding of the penis internally within the condom to produce a rubbing action between the penis and the condom thereby providing a greater sense of feeling on the part of the male, and the condom is rolled for storage, a quantity of a liquid lubricant is placed within the inside thereof, a temporary seal is provided between the condom and a barrier means to hold the lubricant on the inside of the condom and to prevent its migration around the rolled up portion of the condom to the outside surface of the condom.

25. A condom having a sheath-like body with a closed end and an open end, an enlarged diameter in a distal region adjacent to the closed end, a reduced diameter in a proximal region located near the open end, an internally located friction producing agent in the proximal portion and an external friction imparting agency in the distal portion to assist in tending to hold the condom in place within the vagina.

26. A male stimulating condom comprising a condom body having an inside and an outside, means inside the condom during use to promote slippage of the penis therein and means outside of the condom to retard slippage between the vagina and the condom and the means on the outside to retard slippage comprises a dispersion of hydrocolloid particles and an elastic matrix.

27. The condom of claim 26 wherein the particles comprise at least one member selected from the group consisting of guar gum, gum acacia, gum tragacanth, karaya, carboxymethylcellulose, carboxypropylcellulose, polyvinylalcohol, gelatin, powdered pectin or carboxypolymethylene.

28. A packaged condom comprising, a sealed envelope, a rolled latex condom therein having an inside and an outside, a quantity of liquid lubricant inside the condom, a friction imparting agency on the outside of the condom and a barrier releasably sealed across the rolled portion of the condom to prevent the lubricant from reaching said agency.

29. A method of providing a natural feeling condom comprising rolling a condom to form a roll at the edge and to thereby define inside and outside surfaces and an inwardly opening cup on the inside surface, depositing a lubricant within the cup to lubricate the inside of the condom, sealing a sheet of a barrier material to the roll to extend across the cup and cover the cup to prevent the internal lubricant from migrating during storage to the outside surface of the condom whereby the outside surface will not be lubricated to aid in establishing a frictional relationship between the outer surface and the vagina for facilitating movement of the penis during coitus within the condom.

30. The method of claim 29 wherein the barrier sheet is one wall of a packaging envelope enclosing said condom.

31. An improved condom for providing greater penile stimulation comprising, an elongated hollow condom body closed at one end and open at the other end and formed from a supple sheet material, a multiplicity of internal stimulation elements therein and located during use adjacent to or in contact with the penis, said condom being constructed and arranged to permit at least the distal end of the penis to slide internally within the condom to thereby provide a greater stimulation of the penis owing to the motion of the condom relative to the penis and the resultant sliding motion of the stimulation elements over the surface of the penis and the stimulation elements are fibers bonded to the inner surface of the condom.

32. A method for manufacturing a latex condom which comprises, providing a forming mandrel of a predetermined size and shape adapted to form a condom, applying latex rubber to the surface of the mandrel to form said condom, allowing the latex rubber coating on the mandrel to cure to form a sheath conforming to the shape of the mandrel, and applying a friction imparting agency to the outside surface of the condom for establishing a frictional relationship between the condom and the vagina during intercourse, unrolling the sheath from the mandrel to form a rolled latex condom and sealing the rolled latex condom within a container.

33. A method for manufacturing a condom comprising, providing a mandrel of a predetermined size and shape and having a releasing surface, applying a coating of a friction imparting agency to the surface of the mandrel for frictionally relating the condom to the vagina, applying a release layer over the friction imparting agency coating, dipping the coated mandrel into a bath of latex rubber, withdrawing the coated mandrel from the latex rubber, allowing the latex rubber coating on the mandrel to harden to form a sheath having the shape of the mandrel, rolling up the sheath on the mandrel to form a rolled latex condom and packaging the rolled latex condom in a container whereby upon unrolling the condom the friction imparting agency will adhere to the outside surface of the condom due to the contact thereof while in the roll with the cured latex rubber.

34. The method of claim 33 wherein an adhesive layer is applied to said mandrel on a surface area thereof separate from the area covered by said friction imparting agency, an aligned outside portion of the overlying condom formed in said dipping operation is coated with a release coating whereby when said rolled condom is unrolled said adhesive will remain adhered to the inside of the condom and will not transfer to the outside surface thereof while it is rolled up.

35. The condom of claim 20 wherein the hydrocolloid comprises dry particles supported by the elastic matrix.

36. The method of claim 32 wherein an elastic matrix is applied to the outside surface of the condom and the friction imparting agency is applied to the elastic matrix and bonded to the sheath thereby.

37. The method of claim 36 wherein fibers are bonded between the elastic matrix and the friction imparting agency.

38. The condom of claim 18 wherein a vaginal friction enchancing composition is bonded to said fibers.

39. The method of claim 32 wherein the friction imparting agency is a hydrophilic material that produces a viscous layer when exposed to vaginal fluids.

40. A male stimulating condom comprising a flexible sheath having a closed end and an open end adapted to fit tightly around the base of the penis to form a seal thereon, the closed end including a rubbery matrix layer on at least the outside of the sheath and a layer of a hydrophilic natural or synthetic hydrocolloid bonded to the condom by the rubbery matrix and upon exposure to vaginal fluid being adapted to form a friction producing material for stabilizing the condom in the vagina to thereby facilitate movement of the penis within the closed end of the condom.

41. The condom of claim 40 wherein the rubbery matrix is a layer comprising at least one member selected from the group consisting of polyisobutylene, natural rubber latex, acrylonitrile rubber, polyurethane rubber and silicone rubber.

* * * * *